(12) United States Patent
Schiffter et al.

(10) Patent No.: US 10,610,487 B2
(45) Date of Patent: *Apr. 7, 2020

(54) SALTS OF ACTIVE INGREDIENTS WITH POLYMERIC COUNTERIONS

(71) Applicant: BASF SE, Ludwigshafen am Rhein (DE)

(72) Inventors: Heiko Alexander Schiffter, Overath (DE); Maximilian Angel, Kasendorf (DE); Karl Kolter, Limburgerhof (DE); Felicitas Guth, Neustadt (DE)

(73) Assignee: BASF SE, Ludwigshafen (DE)

( * ) Notice: Subject to any disclaimer, the term of this patent is extended or adjusted under 35 U.S.C. 154(b) by 113 days.

This patent is subject to a terminal disclaimer.

(21) Appl. No.: 15/753,186

(22) PCT Filed: Aug. 17, 2016

(86) PCT No.: PCT/EP2016/069457
§ 371 (c)(1),
(2) Date: Feb. 16, 2018

(87) PCT Pub. No.: WO2017/032651
PCT Pub. Date: Mar. 2, 2017

(65) Prior Publication Data
US 2018/0235885 A1 Aug. 23, 2018

(30) Foreign Application Priority Data

Aug. 21, 2015 (EP) .................................... 15181991

(51) Int. Cl.
| | | |
|---|---|---|
| *A61K 9/16* | (2006.01) | |
| *A61K 47/69* | (2017.01) | |
| *A61K 9/20* | (2006.01) | |
| *C08L 39/06* | (2006.01) | |
| *C08L 33/08* | (2006.01) | |
| *A61K 31/00* | (2006.01) | |
| *C08F 220/18* | (2006.01) | |
| *C08F 220/06* | (2006.01) | |
| *C08F 226/10* | (2006.01) | |
| *A61K 31/4515* | (2006.01) | |
| *A61K 31/451* | (2006.01) | |
| *A61K 31/495* | (2006.01) | |
| *A61K 31/426* | (2006.01) | |

(52) U.S. Cl.
CPC .......... *A61K 9/1635* (2013.01); *A61K 9/2027* (2013.01); *A61K 31/00* (2013.01); *A61K 31/426* (2013.01); *A61K 31/451* (2013.01); *A61K 31/4515* (2013.01); *A61K 31/495* (2013.01); *A61K 47/6933* (2017.08); *C08F 220/06* (2013.01); *C08F 220/18* (2013.01); *C08F 226/10* (2013.01); *C08L 33/08* (2013.01); *C08L 39/06* (2013.01); *C08L 2203/02* (2013.01)

(58) Field of Classification Search
CPC .............. A61K 9/1635; A61K 47/6933; A61K 9/2027; C08L 39/06; C08L 33/08
See application file for complete search history.

(56) References Cited

U.S. PATENT DOCUMENTS

| | | |
|---|---|---|
| 4,205,060 A | 5/1980 | Monsimer et al. |
| 4,248,855 A | 2/1981 | Blank et al. |
| 4,853,439 A | 8/1989 | Barabas |
| 4,997,643 A | 3/1991 | Partain, III et al. |
| 5,708,021 A | 1/1998 | Assmus et al. |
| 5,736,127 A | 4/1998 | Stoy et al. |
| 2009/0258953 A1 | 10/2009 | Dobrawa et al. |
| 2010/0280047 A1* | 11/2010 | Kolter .................... A61K 9/146 514/255.04 |

FOREIGN PATENT DOCUMENTS

| | | |
|---|---|---|
| EP | 0 211 268 A2 | 2/1987 |
| EP | 0721785 A2 | 7/1996 |
| WO | WO-2007/141182 A2 | 12/2007 |
| WO | WO-2009/074609 A1 | 6/2009 |

OTHER PUBLICATIONS

International Search Report for PCT Patent Application No. PCT/EP2016/069457, dated Oct. 7, 2016 (translation).
Amidon, et al.,"A Theoretical Basis for a Biopharmaceutic Drug Classification: the Correlation of *in Vitro* Drug Product Dissolution and *in Vivo* Bioavailability," *Pharmaceutical Research* 12, No. 3 (1995), pp. 413-420.
Uelzmann, H., "Copolymers of Acrylic Acid and N-Vinylpyrrolidone-2," *Journal of Polymer Science Part A: Polymer Chemistry* 33, No. 126 (1958), pp. 377-379.

* cited by examiner

*Primary Examiner* — Catherine S Branch
(74) *Attorney, Agent, or Firm* — Marhsall, Gerstein & Borun LLP

(57) ABSTRACT

Water-soluble polymeric salts of medicaments sparingly soluble in water consisting of a cationogenic medicament which, in uncharged form or as hydrochloride, has a solubility of less than 0.1% (m/m) in water, artificial intestinal juice or gastric juice, and an anionogenic water-soluble polymer having a solubility in water of at least 5% (m/m) in the pH range of 1 to 13 and which is obtained by free-radically initiated polymerization of a monomer mixture of i) 70 to 90% by weight N-vinylpyrrolidone and ii) 10 to 30% by weight acrylic acid, wherein the sum total of i) and ii) corresponds to 100% by weight.

17 Claims, No Drawings

SALTS OF ACTIVE INGREDIENTS WITH POLYMERIC COUNTERIONS

CROSS-REFERENCE TO RELATED APPLICATIONS

This application is the U.S. National Stage application of International Patent Application No. PCT/EP2016/069457, filed Aug. 17, 2016, which claims the benefit of European Patent Application No. 15181991.9, filed Aug. 21, 2015.

The present invention relates to solid salts of cationic active ingredients with polymeric anionic counterions.

Numerous medicaments have a very low solubility in water and can consequently not be absorbed from the gastric and intestinal tract. The result is very low bioavailability. For medicaments which have a basic group, corresponding salts can be formed by reaction with acids, said salts sometimes having better solubilities. For this purpose, low molecular weight acids or alkalis are generally used. The most common acids are: hydrochloric acid, sulfuric acid, acetic acid, citric acid, tartaric acid, fumaric acid, maleic acid, malonic acid, succinic acid and phosphoric acid. Often, there is barely any difference between the solubility of the medicament acid or base and that of a salt with the specified compounds. The cause of this poor solubility is usually that the salt forms a very stable crystal lattice which is energetically in a favorable state, as a result of which the tendency to dissolve is low. If, additionally, the energy gain as a result of hydration is low, the solubility is further reduced.

Salts of medicaments with polymeric acids or bases have hitherto already been produced in principle, although polymers were often used which were not soluble over a large pH range—in particular not in the physiologically relevant range of pH 1-8—or which in solution as acid, base or salt, have a high viscosity.

If the polymers have high viscosity in aqueous solution, the active ingredient release from a solid administration form such as, for example, a tablet, is likewise delayed. Upon dissolution of the salt, a gel or a highly viscous solution forms on the surface of the tablet and in the cavities, preventing further penetration of the water into the tablet core and slowing disintegration. This effect and also the reduced diffusion coefficient of the medicament molecules through areas with high viscosity delay the release of the medicament. In this respect, gel-forming polymers are unsuitable for producing rapid-release forms in which a sparingly soluble medicament is to be dissolved quickly and provided to the entire gastric and small intestine surface for absorption.

EP 0211268 describes minoxidil salts with polymeric polyanions which have delayed release and are used for dermal application. Minoxidil is a medicament which comprises 4 groups capable of salt formation and the corresponding polymeric salts were less soluble than the hydrochloride. The numerous groups capable of salt formation greatly reduce the dissociation of the salt and do not improve the solubility compared with the hydrochloride. Oral applications are not described.

U.S. Pat. No. 4,997,643 describes a biocompatible, film-forming delivery system for topical application which comprises a polymeric salt with a carboxyl-group-carrying component. The medicament used is likewise minoxidil, which has the aforementioned special characteristics. Oral applications are not described.

U.S. Pat. No. 4,248,855 claims liquid preparations which comprise salts of basic medicaments and water-insoluble polymers, and which have a slow-release effect. As a result of the use of water-insoluble polymers, the preparations do not exhibit rapid release or high solubility over a large pH range.

It is known from U.S. Pat. No. 5,736,127 that salts may be formed from basic medicaments and polymers obtained by partial hydrolysis of gel-forming polyacrylonitriles. On account of the high molecular weights, the polymers are gel-forming, as a result of which the release of the active ingredients is delayed. Suitability for rapid-release tablets is not stated.

U.S. Pat. No. 4,205,060 describes microcapsules with delayed release which comprise, in the core, a salt of a basic medicament with a carboxyl-group-containing polymer and which is surrounded by a water-insoluble polymer. The carboxyl-group-containing polymer reduces the release of the soluble medicaments used.

Salts of ranitidine with polycarboxylic acids are described in EP 0721785. The polycarboxylic acids bind the ranitidine and are intended to reduce its bitterness. However, low molecular weight salts of ranitidine are readily soluble, meaning that the polycarboxylic acids merely restrict the mobility and diffusion of the ranitidine, meaning that it does not pass so rapidly to the bitter receptors.

WO 2007/141182 describes the use of copolymers of vinyl acetate with acidic monomers comprising sulfonate groups for solubilizing sparingly soluble active ingredients. These copolymers, however, have considerable disadvantages in application owing to the very acidic character of the sulfonate group, since they have rapidly to corrosion of all metallic materials with which they come into contact.

U.S. Pat. No. 4,853,439 describes water-soluble complexes of homopolymers or copolymers of N-vinylpyrrolidone with water-insoluble active ingredients. Among the copolymers described are in very general terms those which may comprise acid group-containing monomers such as acrylic acid. Specifically described, however, is only a copolymer with maleic anhydride which, due to physical characteristics such as color, purity and viscosity, is unacceptable for the pharmaceutical user.

H. Uelzmann, Journal of Polymer Science, Vol. XXXIII, pp 377-379 (1958) describes without details a possible use of relatively high molecular weight copolymers of acrylic acid and N-vinylpyrrolidone with different molar proportions, wherein such copolymers at molar ratios of 1:1 or 1:2 AA:VP are soluble in water although in concentrated form (50% strength by weight). However, when diluted with water to 5% strength by weight mixtures for example, the copolymer precipitates out. The copolymers are also insoluble in dilute hydrochloric acid. Such solubility behavior for application to improvement of solubility of pharmaceutical active ingredients is unacceptable.

Although the homopolymer of N-vinylpyrrolidone has been known for a long time as a polymer matrix for solid solutions of sparingly soluble active ingredients for improving solubility and bioavailability, solid solutions have disadvantages in terms of long-term stability. Solid solutions are frequently insufficiently thermodynamically stable with respect to recrystallization of the active ingredient. Since recrystallization of the active ingredient, however, can have major impacts on the release profile and bioavailability, insufficiently thermodynamically stable systems are disadvantageous from the standpoint of drug safety.

Polymeric active ingredient salts are known from WO 2009/074609 which have a high proportion of acid group-containing monomers. Specifically, polymeric counterions are described comprising at least 80% by weight carboxyl-group-containing monomers such as acrylic acid. It has been shown, however, that these high carboxyl group-containing polymers have disadvantages despite their good solubility in the application. For instance, they have a tendency to decarboxylate under thermal stress. They also have disadvantages with respect to storage stability. Due to the high carboxyl group content, there is a greater risk of interaction of the excess acid groups and thus damage to the active ingredients at sensitive binding sites. In addition to this, depending on the structure of the polymer but in particular in the case of pure polyacrylic acids, the viscosity of an aqueous solution in the preparation of the salts by spray-drying can also be disadvantageous, since either only very dilute solutions can be used or heating is necessary prior to the spraying process in order to obtain a clear spray solution.

Lack of stability of the active ingredient or of the active ingredient salt with respect to degradation or discoloration of the formulations are not acceptable from the perspective of a pharmaceutical company, no more than in the food supplement or animal feed sector or in cosmetics.

It was an object of the present invention to find active ingredient salts which help to avoid the disadvantages of the prior art and, with good stability, permit a more rapid release of the active ingredient compared to the corresponding hydrochloride salt. Furthermore, the sought active ingredient salts should also be soluble irrespective of the pH and concentration.

Accordingly, polymeric salts of active ingredients sparingly soluble in water, consisting of a cationogenic active ingredient which, in uncharged form or as hydrochloride, has a solubility of less than 0.1% (m/m) in water, artificial intestinal juice or gastric juice, and an anionogenic water-soluble polymer having a solubility in water of greater than 10% (m/m) in the pH range of 3 to 11 and which is obtained by free-radically initiated polymerization of a monomer mixture of i) 70 to 90% by weight N-vinylpyrrolidone and ii) 10 to 30% by weight acrylic acid, wherein the sum total of i) and ii) corresponds to 100% by weight, were.

The polymeric salts are water-soluble which means that they have a solubility in water under standard conditions which is greater than that of the corresponding hydrochlorides. In particular, the water solubility is more than 50% higher based on the solubility in water of the hydrochloride.

Furthermore, methods for preparing the polymeric salts and also the use thereof have been found.

Suitable active ingredients in the context of the invention are cationogenic active ingredients sparingly soluble in water.

"Cationogenic" signifies that the active ingredient is capable of forming cations and "sparingly soluble in water" signifies that the active ingredients in the context of the invention are those which in uncharged form or as hydrochloride have solubilities of less than 0.1% (m/m) in water, artificial intestinal juice or gastric juice (at 20+/−5° C. and standard atmospheric pressure of 1013.25 hPa).

In principle, all pharmaceutical active ingredients, nutraceuticals, food or feed additives sparingly soluble in water and having sufficient basicity for salt formation are suitable.

Preferred cationogenic active ingredients have at least one and at most two groups capable of salt formation.

In particular, the cationogenic active ingredients are pharmaceutical active ingredients.

As a result of the described salt formation, it is also possible to dissolve medicaments for which neither the neutral form nor the corresponding low molecular weight salts are soluble in water. For these medicaments, the dissolution in the gastric and intestinal tract is very slow and thus limiting for the absorption, as a result of which low bioavailability often results (according to the Biopharmaceutical Classification System: Class II active ingredients (Amidon et al., Pharm. Res. 12, 413-420)).

The pharmaceutical active ingredients here may be from any indication field.

Examples to be mentioned here include antihypertensives, vitamins, cytostatics, especially taxol, anesthetics, neuroleptics, antidepressants, antibiotics, antimycotics, fungicides, chemotherapeutics, urologics, platelet aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, narcotics, antilipemics, liver therapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, weight loss agents, perfusion promoters, diuretics, diagnostics, corticoids, cholinergics, biliary therapeutics, antiasthmatics, broncholytics, beta-receptor blockers, calcium antagonists, ACE inhibitors, arteriosclerosis remedies, antiphlogistics, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists or antiviral active ingredients or active ingredients for the treatment of HIV infections and AID syndrome.

The anionogenic polymers referred to in accordance with the invention are those which are capable of forming anions. In accordance with the invention, this property is based on the presence of carboxyl groups.

The anionogenic polymers according to the invention are all water-soluble independent of pH in the entire pH range of pH 1 to pH 13. Water-soluble signifies that at least 5% (m/m) polymer is clearly soluble in water. No turbidity is apparent optically in the clear solutions.

In particular, the anionogenic polymers have a solubility in water of greater than 10% (m/m) in the pH range of 3 to 11.

All data on the water solubility refer to all anionogenic polymers used in accordance with the invention under standard conditions of 20+/−5° C. and standard atmospheric pressure of 1013.25 hPa.

The datum (m/m) denotes mass fractions.

The anionogenic polymers according to the invention have no miscibility gaps in the concentration range of 5% by weight to 50% by weight, based on polymer in solvent, in water and in 0.08M hydrochloric acid as solvents. "No miscibility gaps" signifies that the polymers are clearly soluble in the solvent and that no turbidity is thus apparent optically.

The anionogenic polymers used in accordance with the invention form optically clear solutions in water which are also storage-stable. "Storage-stable" signifies that the aqueous polymer solutions on storage at 40° C. and atmospheric pressure in the above-mentioned concentration range have no sediment after six months. "No sediment" signifies that less than 1% by weight of the polymer used in the preparation of the solution precipitates out of the solution. Preference is given to anionogenic polymers which, on storage under the conditions stated in an aqueous solution medium, precipitate less than 0.1% by weight, based on the amount of anionogenic polymer used.

All anionogenic polymers mentioned are non-gel-forming in solvents, particularly in water. Nongel-forming signifies that they do not form three-dimensional networks and therefore comprise no pores into which solvent molecules could penetrate.

The anionogenic polymers have Fikentscher K-values, measured in a 5% by weight aqueous solution, of less than 30, particularly preferably less than 20. This K-value is a characteristic of the viscosity of the solution, which in turn represents a measure of the molecular weight of these polymers. The glass transition temperatures calculated according to the Fox equation are in the range of 140 to 160° C.:

$$\frac{1}{T_G} = \sum_i^n x_i \frac{1}{T_{G,i}}$$

$x_i$=mass fraction of the comonomer in the polymer
$T_{G,i}$=glass transition temperature of the homopolymer of the corresponding comonomer
$T_G$=glass transition temperature of the copolymer The glass transition temperatures may also be measured by differential scanning calorimetry at a heating rate of 20 K/min and are in the range of 130 to 170° C.

As already mentioned, suitable anionogenic water-soluble polymers for water-soluble polymeric salts of active ingredients sparingly soluble in water consisting of a cationogenic active ingredient, which in uncharged form or as hydrochloride has a solubility of less than 0.1% (m/m) in water, artificial intestinal juice or gastric juice, are those polymers having a solubility in water of greater than 10% (m/m) over the entire pH range of 3 to 11 and which are obtained by free-radically initiated polymerization of a monomer mixture of i) 70 to 90% by weight N-vinylpyrrolidone and ii) 10 to 30% by weight acrylic acid, wherein the sum total of i) and ii) corresponds to 100% by weight.

Preference is given to anionogenic polymers having a solubility in water of greater than 10% (m/m) over the entire pH range of 3 to 11 and which are obtained by free-radically initiated polymerization of a monomer mixture of i) 75 to 85% by weight N-vinylpyrrolidone and ii) 15 to 25% by weight acrylic acid, wherein the sum total of i) and ii) corresponds to 100% by weight.

Particular preference is given to using an anionogenic polymer having a solubility in water of greater than 10% (m/m) over the entire pH range of 3 to 11 and which is obtained by free-radically initiated polymerization of a monomer mixture of i) 80% by weight N-vinylpyrrolidone and ii) 20% by weight acrylic acid, wherein the sum total of i) and ii) corresponds to 100% by weight.

The polymers can be prepared in a conventional manner per se by free-radical polymerization. The polymerization is preferably carried out as a solution polymerization in organic solvents, preferably in alcohols, particularly in isopropanol. Such methods are known per se to those skilled in the art. Suitable initiators are, for example, organic peroxides such as tertiary-butyl perpivalate or alcohol-soluble azo starters.

The polymerization can usually be conducted at temperatures of 50 to 130° C. and pressures of 0.1 to 1.5 MPa.

It may also be recommended to carry out the polymerization in the presence of chain transfer agents, for example, sodium hypophosphite.

The polymerization can be carried out continuously or as a batch process, the polymers preferably being obtained via a feed process.

According to one embodiment of the invention, the sodium salt of the copolymer is firstly prepared by free-radical copolymerization of N-vinylpyrrolidone and sodium acrylate, which can then be converted into the free acid copolymer by ion exchange.

The conversion of the polymer solutions into the solid form may also be carried out by conventional processes by means of spray-drying, freeze-drying or roller drying.

According to a particularly preferred embodiment, the polymers have K-values in the range from greater than 10 and less than 20.

During the preparation of the polymers according to the invention, it is preferably to be ensured that these have no low molecular weight anions such as, for example, chloride, sulfate, etc. which can lead to sparingly soluble salts with active ingredients.

According to one embodiment of the invention, the water-soluble salts of active ingredients are obtained by dissolving in an aqueous solution medium an anionogenic polymer soluble in water at pH 1-13 and a cationogenic active ingredient sparingly soluble in water, which in uncharged form or as hydrochloride has a solubility of less than 0.1% (m/m) in water, artificial intestinal juice or gastric juice, and by isolating the polymeric active ingredient salt from the solution. The dissolution medium may also be a solvent mixture. Aqueous dissolution medium signifies that the dissolution medium consists only of water as solvent or is a mixture of water and organic solvent. Suitable organic solvent (mixtures) in the aqueous dissolution medium are those organic solvents which are infinitely miscible with water without forming two separate phases. Particularly suitable are methanol, ethanol, ethanol-isopropanol in a ratio of 9:1, isopropanol, tetrahydrofuran, acetone, acetonitrile or dimethylformamide or mixtures thereof.

According to one embodiment of the invention, the cationogenic active ingredient and the anionogenic polymer are dissolved together only in water in the absence of an organic solvent. The poor solubility of the active ingredient does not obstruct this procedure since the presence of the anionogenic polymer acts to solubilize the active ingredient. The dissolution can also take place at elevated temperatures (30-200° C.) and under pressure.

The solids contents of the solutions are selected such that they are in the range of 5 to 60% by weight, preferably 5 to 40% by weight solids content.

Self-evidently, the polymeric active ingredient salts present in aqueous solution may be processed without drying to liquid pharmaceutical administration forms such as drops, syrups or juices. In this case, the further medicament auxiliaries are generally added directly to the aqueous solution.

According to one embodiment of the invention, the polymeric active ingredient salt is isolated by drying a solution described above. In principle, all types of drying are possible, such as, for example, spray-drying, fluidized-bed drying, drum drying, freeze-drying, vacuum drying, belt drying, roller drying, carrier-gas drying or evaporation.

According to a preferred embodiment of the invention, the solid active ingredient salts are prepared by spray-drying. The solution is in this case atomized in a manner known per se using conventional spraying devices such as single or dual component nozzles or via disks and spray-dried with the aid of a drying gas which may be conducted in cocurrent or countercurrent. Suitable drying gases are gases such as air or preferably nitrogen. The tower input temperature of the drying gas can be in the range of 120 to 200° C., preferably 150 to 170° C. The starting temperature of the drying gas is dependent on the concentration of the spray solution, the tower geometry and the type of active ingredient used.

In principle, the conversions for the salt formation can also be carried out as a wet granulation in a mixer by moistening with water or an aqueous solvent medium. Granules in the wider sense can also be produced by means of wet extrusion with subsequent spheronization. The resulting pellets can then be filled into hard capsules as multiple dosage forms.

According to a further embodiment of the invention, the polymeric medicament salt is obtained from the solution by precipitation as a result of cooling or addition of a nonsolvent. The active ingredient and the polymer are dissolved in water or an organic solvent and then the temperature is rapidly reduced or a nonsolvent miscible with water or the organic solvent is added. This results in precipitation of the polymeric salt, which is then filtered off or centrifuged off and is dried. Suitable nonsolvents are, for example, acetone, isopropanol or n-butanol.

According to a further embodiment of the invention, the polymeric salt is prepared via a solid solution which may be obtained by melt processes. This embodiment is useful when the solubility of the cationogenic active ingredient is too low in aqueous organic dissolution media suitable for the industrial application. According to this embodiment, anionogenic polymer and cationogenic active ingredient can firstly be melted with each other. The melting takes place preferably in an extruder such as a twin-screw extruder. By means of the simultaneous input of temperature and shear forces, the components can be dissolved in the melt and, after cooling, an amorphous solid solution can be obtained in which the active ingredient is present embedded in the polymer matrix dispersed at the molecular level. Which temperature is selected for such melting depends, inter alia, on the melting point of the active ingredient and the melting point of the mixture resulting therefrom.

The solid solution thus obtained is brought into contact with water in a controlled manner in a downstream step in order to achieve the salt formation. This may be carried out by moistening in a fluidized bed, in a one-pot processor (can mixing, granulating and drying), in a mixer-granulator, in a Diosna mixer for example, or in an extruder.

Such a controlled moistening is preferably carried out in a fluidized bed. All customary fluidized bed apparatuses are suitable for this purpose. In this case, the solid solution is initially charged in the fluidized bed and converted into the salt form by spraying with water.

After moistening, the water is again dried off so that the dry solid polymeric salt is formed, and may also optionally be adjusted to a defined residual moisture content. Further auxiliaries may be added to the spray solution if, for example, granulation of the polymeric salt particles is also to be carried out in addition to the moistening. Auxiliaries may also be used which enable modification of the release from the later administration form, generally a tablet or capsule.

Depending on the drying process, the solid polymeric active ingredient salts are obtained as a finely divided powder or granules. Typically, the average particle sizes are in the range of 5 to 500 μm as average volume diameter. The polymeric active ingredient salts according to the invention are always amorphous so that problems are avoided, such as in the case of low molecular weight salts where the amorphous state may convert to a thermodynamically stable crystalline state due to external influences or in the course of storage. The amorphous state of the salts according to the invention is thus a thermodynamically stable state because there is no state lower in energy for such substances. The polymeric salts thus differ in principle from the low molecular weight salts.

The amorphous state of the polymeric active ingredient salts can be established by X-ray powder diffraction. The so-called "X-ray amorphous" state of the polymeric active ingredient salts signifies that the crystalline proportion of the polymeric active ingredient salt is less than 5% by weight.

The amorphous state of the polymeric salts can also by investigated with the aid of a DSC thermogram (Differential Scanning calorimetry). The polymeric salts according to the invention have no melting peaks but only a glass transition temperature. The glass transition temperatures are typically measured at a heating rate of 20 K/min. Which glass transition temperatures are present depends essentially on the cationogenic active ingredient.

Verification of salt formation can be carried out with the aid of microcalorimetry. In the relevant specialist literature, a range of 100 to 500 kJ/mol is specified as typical energy for ion-ion interactions, whereas hydrogen bonds typically have binding energies in the range of 20 to 50 kJ/mol, ion-dipole interactions are in the range of 15 kJ/mol and dipole-dipole or van der Waals' interactions are in the range of 2 kJ/mol.

The enthalpy of solution of the active ingredient-polymer compound may be determined by solution calorimetry. For the solution calorimetry, the various prepared formulations are dissolved in a solvent in order to determine the enthalpy of solution. Depending on the enthalpy of solution, the type of binding can be determined. A substance with ionic bonding must have a different enthalpy of solution from a product having other types of bonding, hydrogen bridges or van der Waals' interactions.

The binding energy may also be determined as so-called isothermal titration calorimetry (ITC) or reaction calorimetry. In this case, a reaction partner is initially charged and a second reaction partner added successively. After each addition step, the resulting temperature change is registered and compensated.

The binding enthalpies determined are in the range of ion-ion interactions. The polymeric active ingredient salts are thus true salts.

The problem frequently occurring in the case of low molecular weight salts, that the salts crystallize poorly or occur with low melting points, which makes handling more difficult, is avoided with the polymeric salts described.

In the course of preparation of the solid dosage forms according to the invention, customary pharmaceutical auxiliaries may optionally be processed at the same time. These take the form of substances of the class of fillers, softeners, solubilizers, binders, silicates and also disintegrants and adsorbents, lubricants, flow agents, dyes, stabilizers such as antioxidants, wetting agents, preservatives, release agents, flavorings or sweeteners, preferably fillers, softeners and solubilizing agents.

The fillers added can be e.g. inorganic fillers such as oxides of magnesium, aluminum or silicon, titanium carbonate or calcium carbonate, calcium phosphates or magnesium phosphates or organic fillers such as lactose, sucrose, sorbitol or mannitol.

Suitable softeners are, for example, triacetin, triethyl citrate, glycerol monostearate, low molecular weight polyethylene glycols or poloxamers.

Suitable additional solubilizers are surface-active substances having an HLB value (Hydrophilic Lipophilic Balance) greater than 11, for example, hydrogenated castor oil ethoxylated with 40 ethylene oxide units (Cremophor® RH 40), castor oil ethoxylated with 35 ethylene oxide units (Cremophor EL), polysorbate 80, poloxamers or sodium lauryl sulfate.

The lubricants used may be stearates of aluminum, calcium, magnesium and tin and also magnesium silicate, silicones and the like.

The flow agents used may be, for example, talc or colloidal silicon dioxide.

Suitable binders are, for example, microcrystalline cellulose.

The disintegrants may be crosslinked polyvinylpyrrolidone or crosslinked sodium carboxymethyl starch. Stabilizers may be ascorbic acid or tocopherol.

Dyes are, e.g. iron oxides, titanium dioxide, triphenylmethane dyes, azo dyes, quinoline dyes, indigotine dyes, carotenoids, in order to color the administration forms, and opacifiers such as titanium dioxide or talc in order to increase the transparency and to save on dyes.

The salts according to the invention can be formulated to give many different administration forms such as, for example, tablets, capsules, granules, powders, drug delivery systems, solutions, suppositories, transdermal systems, creams, gels, lotions, injection solutions, drops, juices, syrups.

The release can be slowed by the addition of thermoplastic release-slowing agents such as polyvinyl acetate homopolymers or formulations of such polyvinyl acetate homopolymers, also by the known delayed release polymers Eudragit® of RS, RL or NE or NM type, based on acrylate. In this manner, reliably slow-release forms of poorly soluble medicaments can be produced.

The polymeric salts according to the invention composed of a polymeric anion component and a cationic active ingredient, have an excellent processability to administration forms, particularly with regard to tabletability. Consequently, it is possible to produce tablets with a diameter of 10 mm and 300 mg in weight which have a fracture resistance of more than 200 N. The polymeric anion therefore acts simultaneously as binder and imparts enormous plasticity to the tablet formulation. By contrast, low molecular weight salts are often very brittle and poorly tabletable.

The polymeric salts of active ingredients according to the invention can be granulated in an excellent manner and compressed to give tablets which, on account of the high solubility in aqueous media, will exhibit extremely rapid active ingredient release. The improved solubility results in considerably improved bioavailability. The solubility is usually 0.05 to 5% (parts by weight of medicament/parts by weight of water). In addition, the bioavailability is very reproducible, i.e. there are relatively slight interindividual fluctuations.

EXAMPLES

Abbreviations/Methods

CD water=completely demineralized water

Percentage data relate to percent by weight unless otherwise specified.

X-ray powder diffractometry measuring instrument: Advance D8 Series 2 equipped with multitube sample changer primary side: Cu anode, divergence slit V20 detector: V20 with Sol-X detector The turbidity was measured according to ISO 7027 by measuring the ratio of scattered light and transmission.

The glass transition temperatures were determined by DSC at a heating rate of 20 K/min.

Example 1

Copolymer of 80% by Weight N-Vinylpyrrolidone (VP) and 20% by Weight Acrylic Acid (AA)

Apparatus:

2 l Reactor equipped with anchor stirrer, reflux condenser, nitrogen inlet (via liquid level) and temperature-controlled oil bath. 2 Feed vessels each 1000 ml. Temperature measurement in the polymerization vessel and in the oil bath via Pt100 sensor.

| Feeds | Amount | Starting material |
|---|---|---|
| Initial charge | 210.0 g | isopropanol |
| | 30.0 g | N-vinylpyrrolidone |
| | 10.6 g | Part of feed 2 |
| Feed 1 | 399.0 g | isopropanol |
| | 210.0 g | N-vinylpyrrolidone |
| | 60.0 g | Acrylic acid |
| Feed 2 | 100.0 g | isopropanol |
| | 6.0 g | tert-butyl perpivalate, 75% strength |

The initial charge was heated to 75° C. internal temperature under a gentle nitrogen stream. On reaching 75° C. internal temperature, the part amount of feed 2 was added. Feed 1 and the residual amount of feed 2 were then started. Feed 1 was metered in over 6 hours and the residual amount of feed 2 was metered in over 9 hours.

The reaction mixture was then subjected to another steam distillation in order to displace the isopropanol solvent.

| | |
|---|---|
| Solids content SC [% by wt.] | 30.5 |
| K-value (5% strength in water) | 16.5 |
| FNU value (5% strength in water) | 0.7 |
| Tg (° C.) | 165 (measured by DSC; calculated 150° C., see above) |
| Isopropanol (ppm) | 2800 |

Appearance: water-clear low viscosity aqueous solution.

Example 2

This was carried out as in Example 1 except feed 1 was metered in over 4 hours and the residual amount of feed 2 over 6 hours.

After feed 2 was complete, the polymerization was continued for 1 hour at an internal temperature of 75° C.

| | |
|---|---|
| SC (% by weight) | 30.8 |
| K-value (5% strength in water) | 17.8 |
| FNU value (5% strength in water) | 0.6 |
| Tg (° C.) | 164 (DSC, 20 K/min) |
| Isopropanol (ppm) | 2600 |

Appearance: water-clear low viscosity aqueous solution.

Example 3

Copolymer of 70% by Weight VP and 30% by Weight AA

The preparation was carried out analogously to Example 1, wherein feed 1 comprised 180 g of vinylpyrrolidone and 90 g of acrylic acid.

| | |
|---|---|
| SC (% by weight) | 30.4 |
| K-value (5% strength in water) | 15.8 |
| FNU value (5% strength in water) | 1.5 |
| Tg (° C.) | 144 (calculated) |
| Isopropanol (ppm) | 2200 |

Appearance: water-clear low viscosity aqueous solution.

Example 4

Copolymer of 90% by Weight VP and 10% by Weight AA

The preparation was carried out analogously to Example 1, wherein feed 1 comprised 240 g of vinylpyrrolidone and 30 g of acrylic acid.

| | |
|---|---|
| SC (% by weight) | 30.3 |
| K-value (5% strength in water) | 16.7 |
| FNU value (5% strength in water) | 0.6 |
| Tg (° C.) | 156 (calculated) |
| Isopropanol (ppm) | 2500 |

Appearance: water-clear low viscosity aqueous solution.

Example 5

Copolymer of 85% by Weight VP and 15% by Weight AA

The preparation was carried out analogously to Example 1, wherein feed 1 comprised 225 g of vinylpyrrolidone and 45 g of acrylic acid.

| | |
|---|---|
| SC (% by weight) | 30.5 |
| K-value (5% strength in water) | 16.4 |
| FNU value (5% strength in water) | 0.7 |
| Tg (° C.) | 153 (calculated) |
| Isopropanol (ppm) | 2100 |

Appearance: water-clear low viscosity aqueous solution.

Comparative Example A

Copolymer of 50% by Weight VP and 50% by Weight AA

The preparation was carried out analogously to Example 1, wherein feed 1 comprised 120 g of N-vinylpyrrolidone and 150 g of acrylic acid.

| | |
|---|---|
| SC (% by weight) | 31.5 |
| K-value (5% strength in water) | 12.8 |
| FNU value (5% strength in water) | 3.1 |
| Tg (° C.) | 132 (calculated) |

The polymer thus obtained having an FNU value of 3.1 was no longer "water-clear" on visual inspection but slightly cloudy.

Example 6

Preparation of Active Ingredient Salts by Spray-Drying 750 g of the copolymer VP/AA (80/20) according to Example 1 together with 83.3 g of haloperidol (base) were weighed into 6524.7 g of water and dissolved at room temperature with stirring.

The solution had a total solids content of 11.3% by weight. The solution was subsequently spray-dried in a laboratory spray tower under the following conditions:

drying gas: nitrogen; 30 Nm$^3$/h
inlet temperature: 155° C.
outlet temperature: 75° C.
atomization nozzle: 1.4 mm dual component nozzle
atomizing gas/atomizing pressure: nitrogen/0.2 MPa abs.
liquid flow rate: 452.2 g/h
product separator: cyclone Properties of the spray-dried haloperiodol-VP/AA polymeric salt after spray-drying from aqueous solution:

| | |
|---|---|
| Residual moisture content (measured at 105° C.) | 3.38% by weight |
| Medicament content (measured, UV/VIS at 248 nm) | 11.1% by weight |
| Medicament state (XRD) | X-ray amorphous |

Glass transition temperature 151° C. (no melting point) measured at a heating rate of 20K/min Neither in the DSC thermogram nor in the X-ray diffractometry were crystalline active ingredient fractions seen.

The release of the active ingredient from the spray-dried polymeric salt was determined in CD water. The initial weight was calculated on 100 mg of haloperidol per 250 ml of release medium. The polymeric salt correspondingly weighed out or the pure crystalline substance weighed out were filled into hard gelatine capsules. The following Table and also the graphical depiction show the results of the release of haloperidol from the polymeric salt compared to the crystalline medicament.

| | | |
|---|---|---|
| Release of polymeric haloperidol-VP/AA salt (prepared from aqueous solution) in CD water | 0 min | 0% |
| | 2 min | 0.5% |
| | 4 min | 10.0% |
| | 6 min | 40.5% |
| | 8 min | 77.2% |
| | 10 min | 92.8% |
| | 30 min | 96.3% |
| | 60 min | 95.8% |
| | 120 min | 95.8% |
| Crystalline haloperidol in demineralized water | 0 min | 0.0% |
| | 2 min | 0.1% |
| | 4 min | 0.2% |
| | 6 min | 0.3% |
| | 8 min | 0.4% |
| | 10 min | 0.6% |
| | 30 min | 1.5% |
| | 60 min | 1.8% |
| | 120 min | 2.3% |

Determination of the Saturation Solubilities

To determine the improvement of the saturation solubility of medicament bases by the synthesized VP/AA copolymers, 150 ml of a 15% (m/m) solution of each copolymer was prepared in CD water From each of the prepared solutions, 7 glass penicillin vials having a nominal volume of 50 ml were each filled with 20 g of the copolymer solution. The remaining residual polymer solution was discarded.

To determine the saturation solubility, the sediment method was used. An excess of medicament was added to 20 g of the polymer solution and the mixture was then stirred for 72 h on a magnetic stirrer at room temperature. At the end of the stirring period, the undissolved medicament was removed by means of membrane filtration (pore size 0.45 μm) and the clear filtrate was analyzed by UV spectrophotometry for the amount of dissolved medicament.

The concentration of the medicament present in solution was determined by UV spectrophotometry at the wavelengths listed below:

cinnarizine, $\lambda_{max}$=254 nm famotidine, $\lambda_{max}$=288 nm
loperamide, $\lambda_{max}$=262 nm
haloperidol, $\lambda_{max}$=248 nm If the absorption was too high, the clear filtrate had to be diluted with a suitable solvent (mixture of phosphate buffer pH 7.0 and methanol in a 1:1 ratio) prior to the measurement. A 15% (m/m) solution of the copolymer correspondingly used in the same solvent without medicament served as a blank comparative sample. Using a specific calibration curve that was created separately for each medicament, the saturation solubility was determined in g medicament per 100 ml solution.

Results for the investigation of the saturation solubility of medicaments in water, 0.1M HCl and in a 15% (m/m) solution of the copolymer of VP and AA with various mass ratios. The copolymer was synthesized as direct acid form in isopropanol with subsequent exchange of the solvent for water.

To better differentiate the copolymers, a mean performance compared to 0.1M HCl was calculated using the following formula and listed in the Table below:

$$\text{Performance} = \frac{1}{n} \cdot \sum_{i=1}^{n} \left( \frac{C_{S(API-Polymer)}}{C_{S(API-HCl)}} \right)_i$$

n number of medicaments
$C_{S(API-Polymer)}$ saturation solubility of the medicament in the 15% (m/m) polymer solution
$C_{S(API-HCl)}$ saturation solubility of the medicament in a 0.1M HCl Determination of the binding type in a polymeric loperamide salt.

Here, an inventive salt of loperamide and the copolymer according to example 1, prepared as described in example 6, was compared with a solid solution of loperamide and the identical copolymer and also with a solid solution of loperamide and PVP K17. The solid solution of loperamide and copolymer was obtained by evaporation of a solution of the substances in THF/methanol. The solid solution of loperamide and PVP likewise obtained by evaporation of a solution of the substances in THF/methanol. To prepare the organic solutions, 900 mg of polymer were dissolved with 100 mg of active ingredient in 4.5 g of THF and 4.5 g of methanol such that the solids concentration of the solution was 10% by weight and the active ingredient loading of the solid solution produced was 10% by weight. The values were selected so that a comparison was possible with the spray-dried polymeric salt with loperamide.

The solution was dried in a vacuum drying cabinet (Heraeus Type VT 5042 EK) for 72 hours at a temperature of 50° C. a pressure of 10 mbar. The resulting were then ground to a powder in a laboratory mill (Tube mill control, IKA). The solid solutions were X-ray amorphous.

Reaction Calorimetry

A Nano ITC (Isothermal Titration Calorimeter) from TA Instruments was used for the investigations. The respective polymer was initially charged in the measuring cell. Loperamide was successively added thereto. Once a reaction takes place, the temperature of the sample changes.

This temperature difference was registered and compensated via a Peltier element. The electrical energy required for the compensation was recorded. This amount of energy is in sum identical to the amount of heat of reaction produced or consumed.

| | Saturation solubility in g/100 ml of | | | | Performance in comparison to |
|---|---|---|---|---|---|
| Substance | Cinnarizine | Famotidine | Loperamide | Haloperidol | 0.1M HCl |
| Water | $0.09 * 10^{-3}$ | 0.10 | $7.23 * 10^{-3}$ | $0.26 * 10^{-3}$ | — |
| 0.1M HCl | 0.21 | 3.21 | 0.02 | 0.06 | 1.0 |
| VP/AA (90/10) | 0.27 | 5.00 | 1.77 | 2.88 | 34.8 |
| VP/AA (85/15) | 0.36 | 6.92 | 2.31 | 3.48 | 44.3 |
| VP/AA (80/20) | 0.53 | 6.98 | 2.75 | 3.57 | 50.4 |
| VP/AA (70/30) | 0.51 | 5.59 | 1.61 | 1.57 | 36.9 |

For comparison

| | Saturation solubility in g/100 ml of | | | | Performance in comparison to |
|---|---|---|---|---|---|
| Substance | Cinnarizine | Famotidine | Loperamide | Haloperidol | 0.1M HCl |
| 0.1M HCl | 0.21 | 3.21 | 0.02 | 0.06 | 1.0 |
| VP/AA (80/20) | 0.53 | 6.98 | 2.75 | 3.57 | 50.4 |
| PVP K30 | 0.03 | 0.69 | 0.25 | 0.36 | 4.7 |
| Precipitation polymer MSA/VP (50/50) | 0.00 | 0.00 | 0.47 | 0.00 | 5.9 |
| Solution polymer MSA/VP (50/50) | 0.25 | 0.00 | 0.28 | 0.00 | 3.8 |

The measuring cell and reference cell were embedded in a highly stable temperature-controlled bath (+−0.0002 K at 25° C.). Stirring was provided during the experiment.

Due to the low amounts of heat which are measured here, it is necessary to carry out reference measurements. In these cases, the dilution reaction of the polymers. The amount of heat measured during the dilution reaction was subtracted from the original measurement. The value obtained is the enthalpy of reaction of the active ingredient-polymer reaction.

To determine the enthalpy of reaction, the polymers were each prepared at a concentration of 3 g/L and 1 ml initially charged in each case. The loperamide base was prepared at a concentration of 25 mg/l and added in 5 μl steps. After each addition, there was a pause of 600 s until the reaction had ended. Measurement was at 25° C. A water/ethanol mixture (9:1) served as solvent.

The polymers were initially charged in large excess so that it was ensured that each molecule added could find a corresponding reaction partner.

Solution Calorimetry

This investigation was carried out using a TAM III with SolCal insert from TA instruments. The solvent was initially charged therefor. The sample to be dissolved was hermetically sealed in a glass ampoule. The ampoule was introduced into the solvent and the temperature equilibrated. The solution calorimetry was carried out at 25° C. (nominal temperature).

In a next step, the operating temperature was brought to a temperature in the range of 0.3K below the nominal temperature. Then, the equalization of the operating temperature to the nominal temperature was measured, the curve shape determined and calibrated by specific energy input (electrical energy=thermal energy). The formulations were weighed (20-140 mg) into a snap-off ampoule and introduced into 100 ml of a mixture of water/ethanol in a ratio by volume of 9:1.

The ampoule was then broken on a spike in the measuring cell. The substance to be measured was thereby released in the solvent. After subtraction of the baseline of the temperature profile and the conversion of the temperature to the corresponding amount of heat, a heat flow curve of amount of heat vs. time was obtained. After integration of the curve and reference to the molecular weights, the enthalpy of solution of the substance to be investigated was obtained.

The heat of dissolution of all samples was determined in duplicate. The enthalpy of the polymer, which was determined in a separate measurement, was subtracted proportionally from the heat of solution of the formulation.

The table below shows the results of the measurements of the enthalpy of solution of the individual loperamide-polymer formulations. Column A shows is the total amount of heat $Q_{Tot}$ for the respective formulation. Column B shows the proportional amount of heat of the polymer $Q_{Poly}$. The difference gives the amount of heat $Q_{API}$ of the active ingredient based on the total initial weight (column C) or based on the proportion of the active ingredient (column D). The value in column E is the enthalpy of solution or enthalpy of binding (delta H) of the loperamide.

| | A<br>$Q_{tot}$<br>J/g* | B<br>$Q_{Poly}$<br>J/g* | C<br>$Q_{API}$<br>J/g* | D<br>$Q_{API}$<br>J/g** | E<br>Delta H<br>kJ/mol |
|---|---|---|---|---|---|
| 10.4% loperamide base VP/AA obtained from demin. water | 263 | 202 | 61 | 586 | −279 |
| 32.92% loperamide base VP/AA obtained from THF/methanol | 154 | 151 | 3 | 8 | −4 |
| 10% loperamide/PVP K17 solid solution | 241 | 235 | 6 | 57 | −27 |
| Polymer VP/AA 80/20 | 226 | | | | |
| Kollidon ® 17 (PVP K17) | 261 | | | | |

*based on total initial weight
**based on proportion of active ingredient

The invention claimed is:

1. A water-soluble polymeric salt of a medicament sparingly soluble in water consisting of a cationogenic medicament which, in uncharged form or as hydrochloride, has a solubility of less than 0.1% (m/m) in water, artificial intestinal juice, or gastric juice, and an aniono-genic water-soluble polymer having a solubility in water of at least 5% (m/m) in the pH range of 1 to 13 and which is obtained by a free-radically initiated polymerization of a monomer mixture of i) 70 to 90% by weight N-vinylpyrrolidone and ii) 10 to 30% by weight acrylic acid, wherein the sum total of i) and ii) corresponds to 100% by weight.

2. The water-soluble polymeric salt according to claim 1, wherein the anionogenic polymer is non-gel-forming.

3. The water-soluble polymeric salt according to claim 1, wherein the medicament has at least one and at most two groups capable of salt formation.

4. The water-soluble polymeric salt according to claim 1, wherein the water-soluble salt has a higher water solubility than the medicament and the corresponding hydrochloride of the medicament.

5. The water-soluble salt according to claim 1, wherein the anionogenic polymer in 5% by weight aqueous solution has a Fikentscher K-value of less than 30.

6. The water-soluble salt according to claim 1, wherein the anionogenic poly-mer in 5% by weight aqueous solution has a Fikentscher K-value of less than 20.

7. The water-soluble polymeric salt according to claim 1, comprising an anionogenic polymer obtained by the free-radically initiated polymerization of a monomer mixture of i) 75 to 85% by weight N-vinylpyrrolidone and ii) 15 to 25% by weight acrylic acid, wherein the sum total of i) and ii) corresponds to 100% by weight.

8. The water-soluble polymeric salt according to claim 1, comprising an anionogenic polymer obtained by the free-radically initiated polymerization of a monomer mixture of i) 80% by weight N-vinylpyrrolidone and ii) 20% by weight acrylic acid, where-in the sum total of i) and ii) corresponds to 100% by weight.

9. The water-soluble polymeric salt according to claim 1 comprising an anionogenic polymer which has a solubility in water of greater than 10% (m/m) in the pH range of 3 to 11.

10. The water-soluble salt according to claim 1 comprising anionogenic polymers which have no miscibility gaps in the concentration range of 5% by weight to 50% by weight, based on polymer in solvent, in water and in 0.08M hydrochloric acid as solvents.

11. A method for preparing a water-soluble polymeric salt of a medicament according to claim 1, wherein an anionogenic polymer water-soluble at pH 1-13 and a sparingly soluble cationogenic active ingredient are dissolved in an aqueous solvent at pH 1-13 and the polymeric medicament salt is isolated from the solution.

12. The method according to claim 11, wherein the polymeric active ingredient salt is isolated from the solution by drying.

13. The method according to claim 11, wherein the polymeric medicament salt is obtained from the solution by precipitation as a result of cooling or addition of a nonsolvent.

14. A method for preparing a water-soluble polymeric salt of a medicament according to claim 1, wherein anionogenic polymer and sparingly soluble cationogenic active ingredient are firstly converted into a solid solution and salt formation is brought about by a controlled moistening of the solid solution with water.

15. A dosage form comprising a water-soluble polymeric salt of a medicament sparingly soluble in water, consisting of a cationogenic medicament which, in uncharged form or as hydrochloride, has a solubility of less than 0.1% (m/m) in water, artificial intestinal juice, or gastric juice, and an anionogenic water-soluble polymer having a solubility in water of greater than 5% (m/m) in the pH range of 1 to 13 and which is obtained by a free-radically initiated polymerization of a monomer mixture of i) 70 to 90% by weight N-vinylpyrrolidone and ii) 10 to 30% by weight acrylic acid, wherein the sum total of i) and ii) corresponds to 100% by weight.

16. The dosage form according to claim 15 additionally comprising pharmaceutical auxiliaries.

17. The dosage form according to claim 15 prepared by compression.

* * * * *